United States Patent [19]

Craig et al.

[11] Patent Number: 5,393,773
[45] Date of Patent: Feb. 28, 1995

[54] METHOD FOR THE INTRANASAL ADMINISTRATION OF 3-[2-(DIMETHYLAMINO)-ETHYL]-H-METHYL-1H-INDOLE-5-METHANESULPHONAMIDE

[75] Inventors: Joanne Craig; David A. Saynor, both of Ware, Great Britain

[73] Assignee: Glaxo Group Limited, London, England

[21] Appl. No.: 84,235

[22] PCT Filed: Jan. 19, 1992

[86] PCT No.: PCT/EP92/00094
§ 371 Date: Jul. 12, 1993
§ 102(e) Date: Jul. 12, 1993

[87] PCT Pub. No.: WO92/12712
PCT Pub. Date: Aug. 6, 1992

[30] Foreign Application Priority Data

Jan. 24, 1991 [GB] United Kingdom ............... 9102579

[51] Int. Cl.⁶ .......................................... A61K 31/405
[52] U.S. Cl. ....................................................... 514/415
[58] Field of Search .......................................... 514/415

[56] References Cited

U.S. PATENT DOCUMENTS 5,037,845 8/1991 Oxford ............................... 514/415

FOREIGN PATENT DOCUMENTS 0187433 7/1986 European Pat. Off. .
0358234 3/1990 European Pat. Off. .
2568571 2/1986 France .
2133691 8/1984 United Kingdom .

Primary Examiner—Raymond J. Henley, III
Assistant Examiner—T. J. Crires
Attorney, Agent, or Firm—Bacon & Thomas

[57] ABSTRACT

A method of treating a human suffering from or susceptable to cephalic pain by intramasally administering 3-[2-(dimethylamino)ethyl]-N-methyl-1H-indol-5-methanesulphonamide in a pH range of from 9–11.

16 Claims, No Drawings

METHOD FOR THE INTRANASAL ADMINISTRATION OF 3-[2-(DIMETHYLAMINO)-ETHYL]-H-METHYL-1H-INDOLE-5-METHANESULPHONAMIDE

The present invention relates to a pharmaceutical composition containing as active ingredient 3-[2-(dimethylamino)ethyl]-N-methyl-1H-indole-5-methanesulphonamide, in particular a composition for intranasal administration.

3-[2-(dimethylamino)ethyl]-N-methyl-1H-indole-5-methanesulphonamide, which may be represented by the formula (I)

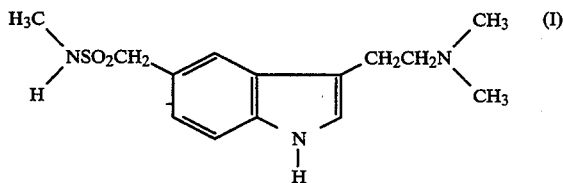

and its physiologically acceptable salts and solvates are disclosed in UK Patent Specification No. 2162522. The compound of formula (I) exhibits selective vasoconstrictor activity and is useful in the treatment of migraine.

Oral compositions have certain disadvantages for the administration of anti-migraine agents. Thus, for example, one of the symptoms associated with migraine is nausea, and the presence of nausea may make it difficult for a patient to take an oral composition. Also, it is desirable that the anti-migraine drug should be rapidly absorbed into the bloodstream. Such rapid absorption can be achieved using intranasal or parenteral administration, but some patients dislike parenteral administration, particularly if the drug is to be self-administered. Intranasal administration therefore represents a preferred route for administration of the compound of formula (I).

We have now found a particularly advantageous formulation for the intranasal administration of the compound of formula (I) comprising an alkaline suspension of the compound of formula (I) or a physiologically acceptable salt or solvate thereof.

There is thus provided according to the invention a pharmaceutical composition in a form adapted for intranasal administration comprising a suspension of 3-[2-dimethylamino)ethyl]-N-methyl-1H-indole-5-methanesulphonamide or a suitable physiologically acceptable salt or solvate thereof as active ingredient wherein the pH is in the range of 8 to 12.

Suitable physiologically acceptable salts and solvates of 3-[2-(dimethylamino)ethyl]-N-methyl-1H-indole-5-methanesulphonamide for use in the present invention are those which have relatively low aqueous solubility, e.g. the succinate and hydrochloride salts. Preferably the pharmaceutical compositions according to the invention contain 3-[2-(dimethylamino)ethyl]-N-methyl-1H-indole-5-methanesulphonamide in the form of the free base.

For satisfactory intranasal administration, an active ingredient must be presented in a form which is readily absorbed through the nasal mucosa but which is unassociated with any adverse effects such as irritancy. Satisfactory intranasal formulations must also be sufficiently stable, chemically and physically, to be consistently dispensed in accurate metered doses, even after prolonged storage with potential temperature fluctuations of between 0° and 400° C. Accordingly, the active ingredient must be compatible with the excipients used in the formulation and should not aggregate in a manner which would result in a loss of accurate dose delivery.

Surprisingly, we have found that suspensions of 3-[2-(dimethylamino)ethyl]-N-methyl-1H-indole-5-methanesulphonamide and suitable physiologically acceptable salts and solvates thereof having a pH in the range of 8 to 12 have excellent dispersion properties. In contrast, neutral and acidic formulations containing such active ingredients do not form readily dispersible suspensions and are unsuitable for use as suspensions for intranasal administration.

Preferably the pH of suspensions according to the invention will be in the range of 9 to 11; most preferably the pH of the suspensions according to the invention will be about 10.

Suspensions will generally be aqueous, for example prepared from water alone (for example sterile or pyrogen-free water) or water and a physiologically acceptable non-aqueous vehicle (for example ethanol, propylene glycol, polyethylene glycols such as PEG 400).

Such suspensions may additionally contain other excipients, for example preservatives (such as benzalkonium chloride and phenylethylalcohol), wetting agents/surfactants such as polysorbates (e.g. Tween 80) and sorbitan esters (e.g. Span 80), buffering agents, isotonicity-adjusting agents (e.g. sodium chloride), suspending agents, absorption enhancers, flavouring agents and sweetening agents (e.g. saccharin).

Preferably suspensions according to the invention will be sterile and free from preservatives. Sterile formulations may be prepared by methods known in the art, for example by aseptic manufacture or sterilisation of the bulk products.

Preferably suspensions according to the invention will be thickened by addition of a viscosity enhancer such as acacia, bentonite, carboxymethylcellulose sodium, gelatin, guar gum, hydroxyethylcellulose, hydroxypropylmethylcellulose, methylcellulose, or tragacanth. The viscosity enhancer may be present in an amount of about 0.1 to about 5% w/w, preferably 0.5 to 2% w/w. Most preferably the viscosity enhancer used will be microcrystalline cellulose with sodium carboxymethylcellulose, e.g. Avicel RC591.

Most preferably suspensions according to the invention will be thixotropic. Thixotropic suspensions can be obtained by the use of a suitable viscosity enhancer e.g. Avicel RC 591.

In a particularly preferred aspect the invention provides a suspension of 3-[2-(dimethylamino)ethyl]-N-methyl-1H-indole-5-methanesulphonamide or a suitable physiologically acceptable salt or solvate thereof and microcrystalline cellulose with sodium carboxymethylcellulose adapted for intranasal administration wherein the pH is in the range of 8 to 12.

Suspensions are applied directly to the nasal cavity by conventional means, for example with a dropper, pipette or spray. The formulations may be provided in single or multidose form. In the latter case a means of dose metering is provided. In the case of a dropper or pipette this may be achieved by the patient administering an appropriate, predetermined volume of the suspension. In the case of a spray this may be achieved for example by means of a metering atomising spray pump.

Intranasal administration may also be achieved by means of an aerosol formulation in which the compound is provided in a pressurised pack with a suitable propellant such as a chlorofluorocarbon (CFC) for example dichlorodifluoromethane, trichlorofluoromethane or dichlorotetrafluoroethane, a hydrofluorocarbon (HFC) for example 1,1,1,2-tetrafluoroethane or 1,1,1,2,3,3,3-heptafluoropropane, carbon dioxide or other suitable gas. The aerosol may conveniently also contain a surfactant such as lecithin. The dose of drug may be controlled by provision of a metered valve.

Preferably a pharmaceutical composition according to the invention will be in the form of an aqueous suspension.

Suspensions according to the invention may be prepared from solutions or suspensions of 3-[2-(dimethylamino)ethyl]-N-methyl-1H-indole-5-methanesulphonamide or suitable physiologically acceptable salts or solvates thereof, by addition of an appropriate amount of a base, such as an inorganic base, preferably an alkali metal hydroxide, most preferably sodium hydroxide.

Preferably the suspensions of the invention will be prepared by suspending 3-[2-(dimethylamino)ethyl]-N-methyl-1H-indole-5-methanesulphonamide, or a suitable physiologically acceptable salt or solvate thereof, of small particle size in an aqueous vehicle at high pH.

As used herein small particle size means particle size of the order of 10 microns or less, preferably 2 to 5 microns. Such a particle size may be obtained by means known in the art, for example, micronisation.

Suspensions according to the invention will preferably contain 3-[2-(dimethylamino)ethyl]-N-methyl-1H-indole-5-methanesulphonamide in a concentration of 20 mgml$^{-1}$ to 500 mgml$^{-1}$.

A further aspect of the invention provides a method of treating a mammal, including man, suffering from or susceptible to conditions associated with cephalic pain such as cluster headache, chronic paroxysmal hemicrania, headache associated with vascular disorders, headache associated with substances or their withdrawal (for example drug withdrawal), tension headache and in particular migraine which comprises intranasal administration of a pharmaceutical composition comprising a suspension of 3-[2-dimethylamino)ethyl]-N-methyl-1H-indole-5-methanesulphonamide or a suitable physiologically acceptable salt or solvate thereof as active ingredient wherein the pH is in the range of 8 to 12. It will be appreciated that reference to treatment is intended to include prophylaxis as well as the alleviation of established symptoms.

It will be appreciated that the precise therapeutic dose of the active ingredient will depend on the age and condition of the patient and the nature of the condition to be treated and will be at the ultimate discretion of the attendant physician.

However, in general effective doses for the treatment of conditions associated with cephalic pain, for example acute treatment of migraine, will lie in the range of 0.5 to 100 mg, preferably 1 to 60 mg, most preferably 2 to 40 mg of the active ingredient per unit dose which could be administered in single or divided doses, for example, 1 to 4 times per day.

Pharmaceutical compositions according to the invention may conveniently be presented in unit dose form. A convenient unit dose formulation for intranasal administration contains 3-[2-(dimethylamino)ethyl]-N-methyl-1H-indole-5-methanesulphonamide in an amount of from 0.5 mg to 100 mg, preferably 1 mg to 60 mg, most preferably 2 mg to 40 mg, which may be administered to either one or both nostrils.

A preferred unit dose formulation may be provided as a single dose in a sealed unit, for example a vial of glass or plastics material which may be filled and sealed using conventional manufacturing techniques. Alternatively, a sealed vial of plastics material may be produced by form-fill-seal technology. Preferably the vial and the components of the pharmaceutical formulation filled therein are heat stable. The sealed vial may be sterilised, for example by autoclaving at 121° C. for not less than 15 minutes, to provide a sterile device prior to use. Preferably the unit dose volume is 50 to 200 μl, for example 100 μl.

The following non-limiting examples further illustrate the invention.

EXAMPLES 1 and 2

|  | Example 1 | Example 2 |
| --- | --- | --- |
| Compound of formula (I) | 20 mg | 400 mg |
| Microcrystalline Cellulose and Carboxymethylcellulose sodium NF (Avicel RC591) | 10 mg | 10 mg |
| Phenylethyl Alcohol USP | 4 mg | 4 mg |
| Benzalkonium Chloride | 0.2 mg | 0.2 mg |
| Polysorbate 80 BP | 0.5 mg | 0.5 mg |
| Purified Water BP | to 1 ml | to 1 ml |

Microcrystalline cellulose and carboxymethylcellulose sodium (Avicel RC591) is dispersed in water and allowed to hydrate. Compound of formula (I) is mixed with a solution of polysorbate 80 and the resultant slurry added to the Avicel RC591 suspension, phenylethyl alcohol and benzalkonium chloride are added and the suspension made to volume with water.

EXAMPLE 3

Compound of formula (I) 50 mg
0.1M Na$_2$CO$_3$/NaHCO$_3$ buffer, pH 10.55 to 1.0 g The buffer was added to the compound of formula (I) and mixed thoroughly to give a stable suspension, pH 10.5.

EXAMPLES 4 and 5

|  | Example 4 | Example 5 |
| --- | --- | --- |
| Compound of formula (I) | 25 mg | 50 mg |
| Microcrystalline cellulose and carboxymethylcellulose USNF (Avicel RC591) | 15 mg | 15 mg |
| Water for Injections B.P. | to 1 g | to 1 g |

Microcrystalline cellulose and carboxymethylcellulose USNF (Avicel RC591) was dispersed in water and allowed to hydrate. The compound of formula (I) was added, dispersed thoroughly and the mixture made up to weight with water to give a stable suspension with a pH of 10.3.

Lowering the pH of the suspension of Example 4 to pH 7.6 by the addition of 22.5% H$_2$SO$_4$ with stirring resulted in immediate separation of the suspension.

EXAMPLE 6

| | |
| --- | --- |
| Compound of formula (I) | 176.5 mg |

| -continued | |
|---|---|
| Microcrystalline cellulose and carboxymethylcellulose USNF (Avicel RC591) | 8.8 mg |
| Phenylethyl alcohol | 4.0 mg |
| Benzalkonium chloride | 0.2 mg |
| Water for Injections BP | to 1 g |

Microcrystalline cellulose and carboxymethyl cellulose USNF (Avicel RC591) was dispersed in water and allowed to hydrate. The compound of formula (I) was added and dispersed thoroughly. Phenylethyl alcohol and benzalkonium chloride were added and the suspension was made up to weight with water to give a stable uniform suspension with a pH of 10.3.

We claim:

1. A method of treating a human suffering from or susceptible to cephalic pain which comprises intranasal administration of a pharmaceutical composition which comprises an aqueous suspension of 3-[2-(dimethylamino)ethyl]-N-methyl-1H-indole-5-methanesulphonamide in the form of the free base or a suitable physiologically acceptable solvate thereof as active ingredient, wherein the pH of the aqueous suspension is in the range of 9 to 11.

2. A method of treating a human suffering from or susceptible to migraine which comprises intranasal administration of a pharmaceutical composition which comprises an aqueous suspension of 3-[2-(dimethylamino)ethyl]-N-methyl-1H-indole-5-methanesulphonamide in the form of the free base or a suitable physiologically acceptable solvate thereof as active ingredient, wherein the pH of the aqueous suspension is in the range of 9 to 11.

3. A method as claimed in claim 1 wherein the aqueous suspension is thixotropic.

4. A method as claimed in claim 2 wherein the aqueous suspension is thixotropic.

5. A method as claimed in claim 1 wherein the composition further comprises a viscosity enhancer.

6. A method as claimed in claim 2 wherein the composition further comprises a viscosity enhancer.

7. A method as claimed in claim 5 which contains viscosity enhancer in an amount of about 0.1 to about 5% w/w.

8. A method as claimed in claim 6 which contains viscosity enhancer in an amount of about 0.1 to about 5% w/w.

9. A method as claimed in claim 5 wherein the viscosity enhancer is microcrystalline cellulose with sodium carboxymethylcellulose.

10. A method as claimed in claim 6 wherein the viscosity enhancer is microcrystalline cellulose with sodium carboxymethylcellulose.

11. A method as claimed in claim 7 wherein the viscosity enhancer is microcrystalline cellulose with sodium carboxymethylcellulose.

12. A method as claimed in claim 8 wherein the viscosity enhancer is microcrystalline cellulose with sodium carboxymethylcellulose.

13. A method as claimed in claim 1 wherein the active ingredient of the composition is present in a concentration of 20 to 500 mgml$^{-1}$.

14. A method as claimed in claim 2 wherein the active ingredient of the composition is present in a concentration of 20 to 500 mgml$^{-1}$.

15. A method as claimed in claim 1 wherein the pharmaceutical composition is presented in unit dosage form comprising 0.5 to 100 mg of active ingredient.

16. A method as claimed in claim 2 wherein the pharmaceutical composition is presented in unit dosage form comprising 0.5 to 100 mg of active ingredient.

* * * * *